(12) United States Patent
de la Poterie et al.

(10) Patent No.: US 6,254,876 B1
(45) Date of Patent: *Jul. 3, 2001

(54) TRANSFER-RESISTANT COSMETIC COMPOSITION COMPRISING A DISPERSION OF POLYMER PARTICLES IN A LIQUID FATTY PHASE

(75) Inventors: Valérie de la Poterie, Le Chatelet en Brie; Nathalie Mougin, Paris, both of (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/217,808

(22) Filed: Dec. 22, 1998

(30) Foreign Application Priority Data

Dec. 22, 1997 (FR) .................................................. 97 16251

(51) Int. Cl.$^7$ ...................................................... A61K 7/48
(52) U.S. Cl. ........................... 424/401; 424/64; 424/70.1; 514/63; 514/744; 514/937
(58) Field of Search ............................ 424/401, 64, 70.1; 514/744, 63, 937

(56) References Cited

U.S. PATENT DOCUMENTS 5,505,937 * 4/1996 Castrogiovanni et al. .

5,945,095 * 8/1999 Mougin et al. .

FOREIGN PATENT DOCUMENTS

| 709083 | * | 5/1996 | (EP) . |
| 2123290 | * | 2/1984 | (GB) . |
| WO 97/01321 | | 1/1997 | (WO) . |

* cited by examiner

Primary Examiner—Raj Bawa
(74) Attorney, Agent, or Firm—Oblon, Spivak, McClelland, Maier & Neustadt, P.C.

(57) ABSTRACT

A composition suitable for topical application, comprising a liquid fatty phase, at least one dye, and at least 2% by weight, relative to the total weight of the composition, of polymer particles which are dispersed and stabilized at the surface by at least one stabilizer in the liquid fatty phase. The present invention also provides a composition suitable for topical application, comprising a cosmetic, dermatological, hygiene or pharmaceutical liquid fatty phase, at least one active agent selected from the group consisting of cosmetic, dermatological, hygiene and pharmaceutical active agents, and at least 2% by weight, relative to the total weight of the composition, of polymer particles which are dispersed and stabilized at the surface by at least one stabilizer in the liquid fatty phase.

29 Claims, No Drawings

TRANSFER-RESISTANT COSMETIC COMPOSITION COMPRISING A DISPERSION OF POLYMER PARTICLES IN A LIQUID FATTY PHASE

BACKGROUND OF THE INVENTION

1. Field of the Invention

The present invention relates to a composition containing polymer particles which are dispersed in a fatty phase, which is intended in particular for the cosmetics, dermatological, pharmaceutical and hygiene fields. More especially the invention relates to a transfer-resistant composition to care for and/or make up the skin, including both human facial and body skin, mucous membranes such as the lips and the inside of the lower eyelids, or the exoskeleton, such as the eyelashes, the eyebrows, the nails and the hair.

The composition may be in the form of a product cast as a stick or as a dish, such as lipsticks or lip balms, cast foundations, concealer products, eyeshadows or blushers, in the form of a more or less fluid paste or cream, such as fluid foundations or lipsticks, eyeliners, antisun compositions or skin coloring compositions.

2. Description of the Background

Make-up or care products for human skin or lips, such as foundations or lipsticks, generally contain fatty phases such as waxes and oils, pigments and/or fillers and, optionally, additives such as cosmetic or dermatological active agents. They can also contain so-called "pasty" products of supple consistency, which make it possible to obtain colored or non-colored pastes to be applied with a brush.

When these compositions are applied to the skin or the lips, they have the drawback of transferring, i.e. of becoming at least partly deposited, leaving traces on certain supports with which they may come into contact, and in particular a glass, a cup, a cigarette, an item of clothing or the skin. This results in mediocre persistence of the film applied, making it necessary to reapply the foundation or lipstick composition regularly. Moreover, the appearance of these unacceptable traces, in particular on shirt collars, can put certain women off using this type of make-up.

Cosmeticians have been interested for several years in lipstick compositions, and more recently in "transfer-resistant" foundation compositions. Thus, Shiseido describe in JP-A-61-65809, transfer-resistant lipstick compositions containing a siloxysilicate resin (with a three-dimensional network), a volatile silicone oil containing a cyclic silicone chain, and pulverulent fillers. Similarly, Noevier described in JP-A-62-61911, transfer-resistant lipstick, eyeliner and foundation compositions containing one or more volatile silicones combined with one or more hydrocarbon-based waxes.

Although these compositions have improved transfer-resistant properties, they have the drawback of leaving on the lips, after the silicone oils have evaporated off, a film which becomes uncomfortable over time (sensation of drying out and of tightness), which puts a certain number of women off this type of lipstick. In order to improve the feeling of comfort with this type of composition, silicone or non-silicone, non-volatile oils may be added, but, in this case, a loss is incurred in terms of transfer-resistance efficacy.

More recently, Procter & Gamble has described in WO-A-96/36323, mascara compositions of water-in-oil emulsion type which have long staying power, water resistance and do not leave traces. These compositions contain, inter alia, a water-insoluble polymer, generally referred to as a latex, combined with a surfactant of the alkyl- or alkoxydimethicone copolyol type, hydrocarbon-based oils, pigments and fillers, as well as waxes.

Compositions based on silicone oils and on silicone resins, as well as those based on latices, lead to matt colored films. However, women nowadays are looking for products, in particular for coloring the lips, which are shiny. Furthermore, the transfer resistance properties of the films deposited are not perfect. In particular, pressure or pronounced rubbing leads to a decrease in the color of the deposit and to redeposition onto the support placed in contact with these films.

In addition, EP-A-497,144 and FR-A-2,357,244 describe compositions referred to as transfer-resistant, containing a styrene/ethylene/propylene block polymer combined with waxes, light or volatile oils and pigments. These compositions have the drawback of being uncomfortable, of having mediocre cosmetic properties and of being difficult to formulate. Moreover, the transfer-resistance properties of these compositions are very mediocre.

There is thus still a need for a composition which does not have the above drawbacks, and in particular which has total transfer-resistance properties, even during pronounced or intensive rubbing or pressure, a relatively shiny appearance, which meets the desire of female consumers, and does not, over time, dry out the skin or the lips to which it is applied.

SUMMARY OF THE INVENTION

The inventors have observed, surprisingly, that the use of polymer particles which are dispersed in a fatty phase, in a cosmetic, dermatological, pharmaceutical or hygiene composition can give a shiny film which has very good staying power, does not transfer at all and is water-resistant, while at the same time being very pleasant to apply and to wear throughout the day. The film is especially supple, flexible and non-sticky.

Thus, the subject of the present invention is a composition for topical application, comprising a liquid fatty phase and at least one dye, characterized in that it also comprises at least 2% by weight, relative to the total weight of the composition, of polymer particles which are dispersed and stabilized at the surface by at least one stabilizer in the liquid fatty phase.

This composition is, in particular, a cosmetic, dermatological, hygiene or pharmaceutical composition. It thus contains ingredients which are compatible with the skin, mucous membranes, keratin fibers or the exoskeleton.

A subject of the invention is also a composition in the form of a cast product comprising at least one cosmetic, dermatological, hygiene or pharmaceutical liquid fatty phase and at least one wax which is solid at room temperature, characterized in that it also comprises at least 2% by weight, relative to the total weight of the composition, of polymer particles which are dispersed and stabilized at the surface by at least one stabilizer in the liquid fatty phase.

The polymer(s) used in the present invention can be of any nature. It is thus possible to use a radical polymer, a polycondensate or even a polymer of natural origin, and mixtures thereof. The polymer(s) can be chosen by a person skilled in the art on the basis of its properties and depending on the intended subsequent use of the composition. Thus, the polymer may or may not be a film-forming polymer. However, obtaining a film which is totally transfer-resistant is more especially due to the use of a film-forming polymer.

A subject of the invention is also a composition comprising a cosmetic, dermatological, hygiene or pharmaceutical volatile liquid fatty phase, at least 2% by weight, relative to the total weight of the composition, of film-forming polymer particles which are dispersed and stabilized at the surface by at least one stabilizer in the fatty phase, and at least one active agent chosen from cosmetic, dermatological, hygiene and pharmaceutical active agents.

The term "volatile fatty phase" refers to any non-aqueous medium which can evaporate from the skin or the lips in less than one hour.

Another subject of the invention is the use, in a cosmetic composition or for the manufacture of a pharmaceutical composition for topical application in the form of a cast product comprising at least one cosmetic, dermatological, hygiene or pharmaceutical liquid fatty phase and at least one wax which is, in particular, solid at room temperature, of polymer particles which are dispersed and stabilized at the surface by at least one stabilizer in the liquid fatty phase, and which are present in particular in a content of at least 2% by weight, relative to the total weight of the composition, in order to reduce, or even eliminate altogether, the transfer of the film of composition deposited on mucous membranes such as the lips and/or on the skin.

Another subject of the invention is the use, in a cosmetic composition or for the manufacture of a pharmaceutical composition for topical application, of particles of at least one film-forming polymer which are dispersed and stabilized at the surface by at least one stabilizer in a liquid fatty phase, and which are present in particular at a content of at least 2% by weight, relative to the total weight of the composition, in order to reduce, or even eliminate altogether, the transfer of the film of composition deposited on human mucous membranes and/or skin onto a support placed in contact with the film.

Another subject of the invention is the use, in a cosmetic composition or for the manufacture of a pharmaceutical composition for topical application comprising a liquid fatty phase and at least one ingredient chosen from cosmetic, dermatological, hygiene and pharmaceutical active agents, dyes and mixtures thereof, of particles of at least one polymer which are dispersed and stabilized at the surface by at least one stabilizer in the liquid fatty phase, and which are present in particular in a content of at least 2% by weight, relative to the total weight of the composition, in order to reduce, or even eliminate altogether, the transfer of the film of composition deposited on the skin and/or mucous membranes such as the lips.

Another subject of the invention is a cosmetic process to care for or make up the lips or the skin, which consists in applying a cosmetic composition as defined above to the lips or the skin, respectively.

Another subject of the invention is a process for limiting, or even eliminating altogether, the transfer of a make-up or care composition from the skin or the lips onto a support other than the skin and the lips, this composition containing a liquid fatty phase and at least one ingredient chosen from dyes and cosmetic, dermatological, hygiene and pharmaceutical active agents, this process consisting in introducing into the liquid fatty phase particles of at least one polymer which are dispersed and stabilized at the surface by at least one stabilizer in the liquid fatty phase and which are present in particular at a content of at least 2% by weight, relative to the total weight of the composition.

One advantage of the use of a dispersion of particles in a composition of the invention is that the particles remain in the form of elementary particles, without forming aggregates, in the fatty phase, which would not be the case with nanometre-sized inorganic particles. Another advantage of the polymer dispersion is the possibility of obtaining very fluid compositions (of about 130 centipoises), even in the presence of a high polymer content.

Yet another advantage of such a dispersion is that it is possible to calibrate the size of the polymer particles as desired, and to modify their size "polydispersity" during synthesis. It is thus possible to obtain very small particles, which are invisible to the naked eye when they are in the composition and when they are applied to the skin or the lips. This would not be possible with pigments in particulate form, since the way in which they are made does not allow the average particle size to be modified.

It has moreover been observed that the compositions according to the invention have particularly advantageous spreading and adhesion qualities on the skin, semi-mucous membranes or mucous membranes, as well as a pleasant, creamy feel. These compositions also have the advantage of being easy to remove, in particular with a standard make-up-removing milk. This is entirely remarkable since the known compositions with high transfer-resistance properties are very difficult to remove. In general, they are sold with a specific make-up-removing product, which places an additional constraint on the user.

A more complete appreciation of the invention and many of the attendant advantages thereof will be readily obtained as the same becomes better understood by reference to the following detailed description.

DETAILED DESCRIPTION OF THE INVENTION

The compositions according to the invention thus preferably contain a stable dispersion of generally spherical particles of at least one polymer, in a physiologically acceptable liquid fatty phase. These dispersions can especially be in the form of polymer nanoparticles as a stable dispersion in the fatty phase. The nanoparticles are preferably between 5 and 600 nm in size, given that beyond about 600 nm, the particle dispersions become much less stable. This size range includes all specific values and subranges therebetween, including 10, 25, 50, 100, 200, 300, 400 and 500 nm.

Yet another advantage of the polymer dispersion in the composition of the invention is the possibility of varying the glass transition temperature (Tg) of the polymer or of the polymeric system (polymer plus additive of the plasticizer type), and thus of going from a soft polymer to a relatively hard polymer, which allows the mechanical properties of the composition to be adjusted as a function of the intended use.

It is possible to use film-forming polymers which preferably have a low Tg, which is less than or equal to the temperature of the skin. A dispersion is thus obtained which can form a film when it is applied to a support, which is not the case when previously known dispersions of inorganic pigments are used.

The polymers which can be used in the composition of the invention preferably have a molecular weight (weight-average) of about from 2000 to 10,000,000 and a Tg of from −100° C. to 300° C.

This molecular weight range includes all specific values and subranges therebetween, including 5,000, 10,000, 25,000, 50,000, 100,000, 250,000, 300,000, 500,000, 750,000 1,000,000, 2,000,000, 5,000,000 and 8,000,000. This Tg range includes all specific values and subranges therebetween, including −75, −50, −25, −10, −5, 0, 5, 10, 25, 50, 75, 100, 150, 200 and 250° C.

When the polymer has a glass transition temperature which is too high for the intended use, it can be combined with a plasticizer so as to lower this temperature in the mixture used. The plasticizer can be chosen from the plasticizers usually used in the field of application, and in particular from compounds which may be solvents for the polymer.

Among the film-forming polymers, mention may be made of acrylic or vinyl, radical homopolymers or copolymers, which preferably have a Tg of less than or equal to 40° C., and in particular methyl methacrylates optionally copolymerized with acrylic acid.

Among the non-film-forming polymers, mention may be made of optionally crosslinked, vinyl or acrylic, radical homopolymers or copolymers preferably having a Tg of greater than or equal to 40° C., such as polymethyl methacrylate, polystyrene or poly(tert-butyl acrylate).

In a nor-limiting manner, the polymers of the invention can be chosen from the following polymers or copolymers: polyurethanes, polyurethane-acrylics, polyureas, polyurea-polyurethanes, polyester-polyurethanes, polyether-polyurethanes, polyesters, polyesteramides, polyesters containing a fatty chain, alkyds; acrylic and/or vinyl polymers or copolymers; acrylic-silicone copolymers; polyacrylamides; silicone polymers, fluoro polymers, and mixtures thereof.

The liquid fatty phase in which the polymer is dispersed can consist of any cosmetically or dermatologically acceptable and, in general, physiologically acceptable oil, chosen in particular from carbon-based, hydrocarbon-based, fluoro and/or silicone oils of mineral, animal, plant or synthetic origin, alone or as a mixture, provided that they form a homogeneous and stable mixture and provided that they are compatible with the intended use.

The expression liquid fatty phase is intended to refer to any non-aqueous medium which is liquid at room temperature.

Mention may thus be made of hydrocarbon-based oils such as liquid paraffin, liquid petroleum jelly, mink oil, turtle oil, soybean oil, perhydrosqualene, sweet almond oil, beauty-leaf oil, palm oil, grapeseed oil, sesame oil, corn oil, parleam oil, arara oil, rapeseed oil, sunflower oil, cottonseed oil, apricot oil, castor oil, avocado oil, jojoba oil, olive oil or cereal germ oil; esters of lanolic acid, of oleic acid, of lauric acid or of stearic acid; fatty esters, such as isopropyl myristate, isopropyl palmitate, butyl stearate, hexyl laurate, diisopropyl adipate, isononyl isononate, 2-ethylhexyl palmitate, 2-hexyldecyl laurate, 2-octyldecyl palmitate, 2-octyldodecyl myristate or lactate, bis(2-ethylhexyl) succinate, diisostearyl malate, glyceryl triisostearate or diglyceryl triisostearate; higher fatty acids, such as myristic acid, palmitic acid, stearic acid, behenic acid, oleic acid, linoleic acid, linolenic acid or isostearic acid; higher fatty alcohols such as ketanol, stearyl alcohol, oleyl alcohol, linoleyl alcohol, linolenyl alcohol, isostearyl alcohol or octyldodecanol; silicone oils, such as polydimethylsiloxanes (PDMSs), which are optionally phenylated, such as phenyltrimethicones, or which are optionally substituted with aliphatic and/or aromatic groups, optionally fluorinated, or substituted with functional groups such as hydroxyl, thiol and/or amine groups; polysiloxanes modified with fatty acids, fatty alcohols or polyox-yalkylenes, fluorosilicones and perfluoro oils.

Advantageously, one or more oils which are volatile at room temperature and atmospheric pressure and which have, for example, a non-zero vapour pressure at room temperature and pressure, and in particular ranging from $10^{-3}$ to 300 mm Hg, on condition that the boiling point is greater than 30° C., can be used. These volatile oils favor the production of a film with total transfer-resistance properties. After these oils have evaporated, a film-forming deposit is obtained which is supple, non-sticky on the skin or mucous membranes, and which follows the movements of the skin or the lips, respectively, onto which the composition is applied. These volatile oils also make it easier to apply the composition to the skin, mucous membranes and the exoskeleton.

These oils can be hydrocarbon-based oils or silicone oils optionally containing alkyl or alkoxy groups at the end of the silicone chain or pendant on the chain.

As volatile silicone oils which can be used in the invention, mention may be made of linear or cyclic silicones containing from 2 to 7 silicon atoms, these silicones optionally including alkyl or alkoxy groups containing from 1 to 10 carbon atoms, as well as $C_8-C_{16}$ isoparaffins. These volatile oils represent in particular from 30 to 97.99% of the total weight of the composition, and better still from 30 to 75%. These ranges include all specific values and subranges therebetween, including 35, 40, 50, 60, 70, 80, 90 and 95% by weight.

As volatile oils which can be used in the invention, mention may be made in particular of octamethylcyclotetrasiloxane, decamethylcyclopentasiloxoane, hexadecamethylcyclohexasiloxane, heptamethylhexyltrisiloxane, heptamethyloctyltrisiloxane or $C_8-C_{16}$ isoparaffins such as the Isopars, the Permetyls and in particular isododecane.

In one specific embodiment of the invention, the liquid fatty phase is chosen from the group comprising:
  non-aqueous liquid compounds with a global solubility parameter, according to the Hansen solubility space, of less than 17 $(MPa)^{1/2}$,
  or monoalcohols with a global solubility parameter, according to the Hansen solubility space, of less than or equal to 20 $(MPa)^{1/2}$ or mixtures thereof.

The global solubility parameter δ global according to the Hansen solubility space is defined in the article "Solubility parameter values" by Eric A. Grulke in "Polymer Handbook", 3rd edition, Chapter VII, pages 519–559, incorporated herein by reference, by the relationship:

$$\delta = (d_D^2 + d_P^2 + d_H^2)^{1/2}$$

in which
  $d_D$ characterizes the London dispersion forces arising from the formation of dipoles induced during molecular impacts,
  $d_P$ characterizes the Debye interaction forces between permanent dipoles,
  $d_H$ characterizes the forces of specific interactions (hydrogen bonding, acid/base, donor/acceptor, etc. type). The definition of the solvents in the three-dimensional solubility space according to Hansen is described in the article by C. M. Hansen: "The three-dimensional solubility parameters", J. Paint Technol. 39, 105 (1967), incorporated herein by reference.

Among the liquid fatty phases with a global solubility parameter, according to the Hansen solubility space, of less than or equal to 17 $(MPa)^{1/2}$, mention may be made of plant oils formed by fatty acid esters of polyols, in particular triglycerides, such as sunflower oil, sesame oil or rapeseed oil, or esters derived from acids or alcohols with a long chain (i.e. containing from 6 to 20 carbon atoms), in particular esters of formula RCOOR' in which R represents a higher fatty acid residue containing from 7 to 19 carbon atoms and R' represents a hydrocarbon-based chain containing from 3 to 20 carbon atoms, such as palmitates, adipates and benzoates, in particular diisopropyl adipate. Mention may also be made of hydrocarbons, and in particular liquid paraffin, liquid petroleum jelly, hydrogenated polyisobutylene or isododecane, or alternatively "Isopars", volatile isoparaffins. Mention may also be made of silicone oils, such as polydimethylsiloxanes and polymethylplhenylsiloxanes, optionally substituted with aliphatic and/or aromatic groups, which may contain fluorine, or with functional groups, such as hydroxyl, thiol and/or amine groups, and volatile silicone oils, in particular cyclic oils. Mention may also be made of solvents, alone or as a mixture, chosen from (i) linear, branched or cyclic esters containing more than 6 carbon atoms, (ii) ethers containing more than 6 carbon atoms, (iii) ketones containing more than 6 carbon atoms. The expression "monoalcohols with a global solubility parameter, according to the Hansen solubility space of less than or equal to 20 $(MPa)^{1/2}$" is intended to refer to aliphatic fatty alcohols containing at least 6 carbon atoms, the hydrocarbon-based chain containing no substitution group. As monoalcohols according to the invention, mention may be made of oleyl alcohol, decanol, dodecanol, octadecanol and linoleyl alcohol. As non-aqueous medium, mention may also be made of those described in FR-A-2,710,646, incorporated herein by reference.

The choice of non-aqueous medium is made by a person skilled in the art based on the nature of the monomers constituting the polymer and/or based on the nature of the stabilizer, as indicated below.

Furthermore, the liquid fatty phase in which the polymer is dispersed can represent from 30% to 97.99% of the total weight of the composition, and preferably from 30 to 75%. These ranges include all specific values and subranges therebetween, including 35, 40, 50, 60, 70, 80, 90 and 95% by weight.

The polymer dispersion can be manufactured as described in EP-A-749,746, incorporated herein by reference. The polymerization can be carried out in dispersion, i.e. by precipitating the polymer during formation, with protection of the particles formed with a stabilizer.

A mixture is thus prepared comprising the initial monomers as well as a radical initiator. This mixture is dissolved in a solvent, which is referred to in the description hereinbelow as the "synthesis solvent". When the fatty phase is a non-volatile oil, the polymerization can be carried out in an apolar organic solvent (synthesis solvent) after which the non-volatile oil (which must be miscible with the synthesis solvent) is added and the synthesis solvent is distilled off selectively.

A synthesis solvent is thus chosen such that the initial monomers and the radical initiator are soluble therein, and the polymer particles obtained are insoluble therein, such that they precipitate therein as they are formed. In particular, the synthesis solvent can be chosen from alkanes such as heptane, isododecane and cyclohexane.

When the fatty phase chosen is a volatile oil, the polymerization can be carried out directly in the oil, which thus also acts as synthesis solvent. The monomers must also be soluble therein, as must the radical initiator, and the polymer obtained must be insoluble therein.

The monomers are preferably present in the synthesis solvent, before polymerization, in a proportion of 5–20% by weight of the reaction mixture. All of the monomers can be present in the solvent before the start of the reaction, or some of the monomers can be added gradually as the polymerization reaction proceeds.

The radical initiator can be, in particular, azobisisobutyronitrile or tert-butylperoxy-2-ethyl hexanoate.

The polymer particles are surface-stabilized, gradually as the polymerization proceeds, by means of a stabilizer which can be a block polymer, a grafted polymer and/or a random polymer, alone or as a mixture. The stabilization can be achieved by any known means, and in particular by adding the block polymer, grafted polymer and/or random polymer directly during the polymerization.

The stabilizer is preferably also present in the mixture before polymerization. However, it is also possible to add it continuously, in particular when monomers are also added continuously. 2–30% by weight of stabilizer can be used relative to the initial monomer mixture, and preferably 5–20% by weight. These ranges include all specific values and subranges therebetween, including 3, 4, 8, 10, 15, 18, 22, 25 and 28% by weight.

When a grafted and/or block polymer is used as stabilizer, the synthesis solvent is chosen such that at least some of the grafts or blocks on the stabilizing polymer are soluble in the solvent, the rest of the grafts or blocks not being soluble therein. The stabilizing polymer used during the polymerization must be soluble or dispersible in the synthesis solvent. Furthermore, a stabilizer is preferably chosen whose insoluble blocks or grafts have a certain affinity for the polymer formed during the polymerization.

Among the grafted polymers, mention may be made of silicone polymers grafted with a hydrocarbon-based chain; hydrocarbon-based polymers grafted with a silicone chain.

Grafted copolymers having, for example, an insoluble skeleton of polyacrylic type with soluble grafts of polyhydroxystearic acid type: copolymers based on $C_1$–$C_4$, alkyl acrylates or methacrylates and on $C_8$–$C_{30}$ alkyl acrylates or methacrylates, are also suitable.

As block or grafted block copolymers comprising at least one block of polyorganosiloxane type and at least one block of a radical polymer, mention may be made of grafted copolymers of acrylic/silicone type which can be used in particular when the non-aqueous medium is a silicone medium.

As block or grafted block copolymers comprising at least one block of polyorganosiloxane type and at least one block of a polyether, it is possible to use imethicone copolyols, such as those sold under the name "Dow Corning 3225C" by Dow Corning, and lauryl methicones, such as those sold under the name "Dow Corning Q2-5200" by Dow Corning.

As block or grafted block copolymers comprising at least one block resulting from the polymerization of a monomer containing simple or conjugated ethylenic bond(s), and at least one block of a vinyl polymer, mention may be made of block copolymers, in particular of "diblock" or "triblock" type, such as polystyrene/polyisoprene, polystyrene/polybutadiene, such as those sold under the name of "Luvitol HSB" by BASF, of the polystyrene/copoly(ethylene-propylene) type, such as those sold under the name "Kraton" by Shell Chemical Co., or alternatively of the polystyrene/copoly(ethylene-butylene) type.

As block or grafted block copolymers comprising at least one block resulting from the polymerization of a monomer containing ethylenic bond(s) (often referred to in the literature as a hydrogenated or non-hydrogenated diene), and at least one block of an acrylic polymer, mention may be made of poly(methyl methacrylate)/polyisobutylene diblock or triblock copolymers or grafted copolymers with a poly (methyl metllacrylate) skeleton and with polyisobutylene grafts.

As block or grafted block copolymers comprising at least one block resulting from the polymerization of a monomer containing ethylenic bond(s), and at least one block of a polyetllcr, mention may be made of polyoxyethylene/polybutadiene or polyoxyethylene/polyisobutylene diblock or triblock copolymers.

When a random polymer is used as stabilizer, it is chosen so that it has a sufficient amount of groups which make it soluble in the synthesis solvent envisaged.

It is thus possible to use copolymers of $C_1$–$C_4$ alkyl acrylates or methacrylates and of $C_8$–$C_{30}$ alkyl acrylates or methacrylates. Mention may be made in particular of the stearyl methacrylate/methyl methacrylate copolymer.

Preferably, a polymer which covers the particles as completely as possible is chosen as stabilizer, several stabilizing polymer chains then being absorbed onto a polymer particle obtained by polymerization.

In this case, it is preferred to use either a grafted polymer or a block polymer as stabilizer, so as to have better interfacial activity. The reason for this is that the blocks or grafts which are insoluble in the synthesis solvent give a more voluminous covering at the surface of the particles.

Moreover, when the liquid fatty phase comprises at least one silicone oil, the stabilizer is preferably chosen from the group consisting of block or grafted block copolymers comprising at least one block of polyorganosiloxane type and at least one block of a radical polymer or of a polyether or a polyester.

When the liquid fatty phase comprises no silicone oil, the stabilizer is preferably chosen from the group consisting of:

(a) block or grafted block copolymers comprising at least one block of polyorganosiloxane type and at least one block of a radical polymer or of a polyether or a polyester, (b) copolymers of $C_1$–$C_4$ alkyl acrylates or methaciylates and of $C_8$–$C_{30}$ alkyl acrylates or methacrylates, (c) block or grafted block copolymers comprising at least one block resulting from the polymerization of hydrogenated or non-hydrogenated diene, and at least one block of a vinyl or acrylic polymer or of a polyether or a polyester, or mixtures thereof.

The dispersions obtained according to the invention can then be used in a composition, in particular a cosmetic, dermatological, pharmaceutical and/or hygiene composition, such as a care or make-up composition for the skin or the lips, or alternatively a hair composition or an antisun or skin-coloring composition.

Depending on the application, it may be chosen to use dispersions of film-forming polymers or of non-film-forming polymers, in volatile or non-volatile oils.

The composition can comprise, as dye, one or more pulverulent compounds and/or one or more liposoluble dyes, for example in a proportion of from 0.01 to 70% of the total weight of the composition. The pulverulent compounds can be chosen from the pigments and/or pearlescent agents and/or fillers usually used in cosmetic or dermatological compositions. Advantageously, the pulverulent compounds represent from 0.1 to 40% of the total weight of the composition, and better still from 1 to 30%. These ranges include all specific values and subranges therebetween, including 0.2, 0.5, 2, 3, 5, 8, 10, 15, 20, 25 and 35% by weight. The more the amount of pulverulent compounds decreases, the more the transfer-resistance and comfort qualities increase. The fact that the transfer-resistance properties increase as the amount of pulverulent compounds decreases is entirely surprising, since the transfer-resistance properties of the known compositions have, until now, increased with the amount of pulverulent compounds.

Conversely, their discomfort and their dryness on the skin or on mucous membranes increased.

Moreover, the transfer-resistance property increases as the amount of polymer dispersible in the liquid fatty phase increases. In practice, the polymer can represent, as active material, up to 60% (as solids or as active material) of the total weight of the composition. This range for the amount of polymer includes all specific values and subranges therebetween, including 3, 5, 10, 15, 20, 25, 30, 35, 40, 45, 50 and 55% by weight. By using more than 12% by weight of active polymer material in the composition, and up to 60%, a totally transfer-resistant film is obtained. Between 2% and 12% the transfer-resistance effect is appreciable although not, however, total. The transfer-resistance properties can thus be adapted as desired, which was not possible with the known transfer-resistance compositions, without negatively affecting the comfort of the film deposited.

Preferably, the weight ratio of pigment(s) polymer is <1 and even ≦0.9. Preferably, this ratio is ≦0.5. This ratio can go down as low as 0.015. These ranges for the pigment/polymer weight ratio include all specific values and subranges therebetween, such as 0.02, 0.05, 0.1, 0.2, 0.3, 0.4, 0.6, and 0.8. Above 0.5, the film transfers slightly and above 1 the film transfers appreciably. In particular, the inventors have varied the contents of pigments and of polymer. The results are given in Table 1 below.

TABLE 1

| Composition | Polymer of Examples | Isododecane | Pigment | Pigment/Polymer | Transfer |
|---|---|---|---|---|---|
| A | 1 | 98 | 1 | 1 | slightly |
| B | 2 | 97 | 1 | 0.5 | no |
| c | 5 | 94 | 1 | 0.2 | no |
| D | 7 | 92 | 1 | 0.14 | no |
| E | 10 | 89 | 1 | 0.1 | no |
| F | 1 | 96 | 3 | 3 | yes |
| G | 1 | 94 | 5 | 5 | yes |
| H | 2 | 95 | 3 | 1.5 | yes |
| I | 5 | 92 | 3 | 0.6 | yes, slightly |
| J | 6 | 91 | 3 | 0.5 | no |

The composition of the invention can advantageously comprise at least 30% by weight of fatty phase, relative to the total weight of the composition.

Below 30%, a granular and pulverulent texture is obtained. This is undesirable when it is sought to obtain a non-granular, homogeneous, creamy appearance in the form of a gel or a stick.

The pigments can be white or colored, and inorganic and/or organic. Among the inorganic pigments, mention may be made of titanium dioxide, which has optionally been surface-treated, zirconium oxide or cerium oxide, as well as iron oxide or chromium oxide, manganese violet, ultramarine blue, chromium hydrate and ferric blue. Among the organic pigments, mention may be made of carbon black, pigments of D & C type, and lakes based on cochineal carmine or on barium, strontium, calcium or aluminum.

The pearlescent pigments can be chosen from white pearlescent pigments such as mica coated with titanium or with bismuth oxychloride, colored pearlescent pigments such as titanium mica with iron oxides, titanium mica with, in particular, ferric blue or chromium oxide, titanium mica with an organic pigment of the above-mentioned type, and pearlescent pigments based on bismuth oxychloride.

The fillers can be inorganic or organic, and lamellar or spherical. Mention may be made of talc, mica, silica, kaolin, Nylon powders (orgasol from Atochem), poly-β-alanine powder and polyethylene powder, Teflon, lauroyllysine, starch, boron nitride, tetrafluoroethylene polymer powders, hollow microspheres such as Expancel (Nobel Industrie), Polytrap (Dow Corning) and silicone resin microbeads (for example Tospearls from Toshiba), precipitated calcium carbonate, magnesium carbonate and hydrocarbonate, hydroxyapatite, hollow silica microspheres (Silica Beads from Maprecos), glass or ceramic microcapsules, metal soaps derived from organic carboxylic acids containing from 8 to 22 carbon atoms, preferably from 12 to 18 carbon atoms, for example zinc, magnesium or lithium stearate, zinc laurate or magnesium myristate.

The liposoluble dyes are, for example, Soudan red, DC Red 17, DC Green 6, β-carotene, soybean oil, Soudan brown, DC Yellow 11, DC Violet 2, DC Orange 5 and quinoline yellow. They can represent from 0.01 to 20% of the weight of the compositions, and better still from 0.1 to 6%. These ranges include all specific values and subranges therebetween, including 0.02, 0.05, 1, 2, 5, 10 and 15% by weight.

The polymer in the composition of the invention makes it possible to form a film on the skin, the lips and/or mucous membranes, forming a network which traps the dyes and/or the active agents. Depending on the relative amount of dyes used, relative to the amount of stabilized polymer used, it is possible to obtain a more or less shiny and more or less transfer-resistant film.

As cosmetic, dermatological, hygiene or pharmaceutical active agents which can be used in the composition of the invention, mention may be made of moisturizers, vitamins, essential fatty acids, sphingolipids and sunscreens. These active agents are used in the usual amount for man, and in particular at concentrations of from 0.001 to 20% of the total weight of the composition. This range includes all specific values and subranges therebetween, including 0.02, 0.05, 1, 2, 5, 8, 10, 12, 15 and 18% by weight.

Depending on the type of use envisaged, the composition according to the invention can also comprise the constituents conventionally used in the fields considered, which are present in an amount which is suitable for the desired pharmaceutical form.

In particular, it can comprise, besides the liquid fatty phase in which the polymer is stabilized, additional fatty phases which can be chosen from waxes, oils, gums and/or pasty fatty substances, of plant, animal, mineral or synthetic origin, or which are even silicone-based, and mixtures thereof.

Among the waxes which are solid at room temperature, which can be present in the composition according to the invention, mention may be made of hydrocarbon-comprising waxes such as beeswax, carnauba wax, candelilla wax, ouricurry wax, Japan wax, cork fibre wax or sugar cane wax, paraffin wax, lignite wax, microcrystalline waxes, lanolin wax, montan wax, ozokerites, polyethylene waxes, the waxes obtained by Fischer-Tropsch synthesis, hydrogenated oils, fatty esters and glycerides which are solid at 25° C. Silicone waxes can also be used, among which mention may be made of alkyl, alkoxy and/or esters of polymethylsiloxane.

The waxes can be in the form of stable dispersions of colloidal wax particles, as can be prepared according to known methods, such as those in "Microemulsions Theory and Practice", L. M. Prince Ed, Academic Press (1977), pages 21–32, incorporated herein by reference. As wax which is liquid at room temperature, mention may be made of jojoba oil.

The waxes can be present in a proportion of 0–50% by weight in the composition, and better still from 10 to 30%. These ranges include all specific values and subranges therebetween, including 0.02, 0.05, 1, 2, 5, 15, 25, 35, 40 and 45% by weight.

The composition can also comprise any additive usually used in such compositions, such as thickeners, antioxidants, fragrances, preserving agents, surfactants, liposoluble polymers such as polyalkylenes, in particular polybutene, polyacrylates and silicone polymers which are compatible with the fatty phase, as well as polyvinylpyrrolidone derivatives. Needless to say, a person skilled in the art will take care to choose this or these optional complementary compounds, and/or the amount thereof, such that the advantageous properties of the composition according to the invention are not, or are not substantially, adversely affected by the addition envisaged.

In one specific embodiment of the invention, the compositions according to the invention can be prepared in the usual manner by a person skilled in the art. They can be in the form of a cast product and, for example, in the form of a stick or tube, or in the form of a dish which can be used by direct contact or with a sponge In particular, they find an application as a cast foundation, a cast blusher or eye shadow, a lipstick, a lipcare balm or base or a concealer product. They can also be in the form of a supple paste with a dynamic viscosity at 25° C. of about 1 to 40 Pa.s, or alternatively in the form of a gel or a more or less fluid cream. in this case, they can constitute foundations or lipsticks, antisun products or skin-coloring products.

The compositions of the invention are advantageously anhydrous and can contain less than 5% water relative to the total weight of the composition. In this case, they can in particular be in the form of an oily gel, an oily liquid, an oil, a paste or a stick, or alternatively in the form of a vesicle dispersion containing ionic and/or nonionic lipids. These pharmaceutical forms are prepared according to the usual methods of the fields considered.

These compositions for topical application can in particular constitute a cosmetic, dermatological, hygiene or pharmaceutical composition for protecting, treating or caring for the face, for the neck, for the hands or for the body (for example, an anhydrous care cream, an antisun oil or a body gel), a make-up composition (for example, a make-up gel) or an artificial tanning composition.

Having generally described this invention, a further understanding can be obtained by reference to certain specific examples which are provided herein for purposes of illustration only and are not intended to be limiting unless otherwise specified.

EXAMPLES

Example 1: Polymer Dispersion

A dispersion of a non-crosslinked copolymer of methyl acrylate and of acrylic acid in an 85/15 ratio, in isododecane, is prepared according to the method of Example 1 of EP-A-749,746, replacing the heptane with isododecane. A dispersion of poly(methyl acrylate/acrylic acid) particles surface-stabilized in isododecane with a polystyrene/copoly (ethylene-propylene) diblock copolymer sold under the name of Kraton G1701 (Shell), which has a solids content of 22.6% by weight and an average particle size of 175 =(polydispersity: 0.05) and a Tg of 20° C., is thus obtained. This copolymer can form a film.

Example 2: Lipstick

A lipstick in fluid form, with the composition below, is prepared:

| | |
|---|---|
| dispersion according to Example 1 | 90.7 g |
| parleam oil | 2.1 g |
| octyldodecanol | 0.9 g |
| PVP/eicosene | 1.2 g |
| phenyltrimethicone | 2.1 g |
| pigments | 3 g |

The pigments contain a mixture of DC Red 27, DC Red 7, DC Red 36, black iron oxide and brown iron oxide. The pigments/polymer ratio is 0.15.

The composition is prepared by simple mixing of the various constituents at room temperature, after grinding the pigments in the oils. A lipstick which is easy to apply and which gives a comfortable, supple and non-sticky film is obtained. This film is also shiny and totally transfer-resistant. It is completely water-resistant and is removed with a standard make-up removing oil.

A sensory test was carried out with this lipstick on several individuals. The transfer resistance test was carried out under the following conditions: application of the product to the lips, drying in the open air for 2 minutes and then application of the lips against a filter paper. This test is repeated under the same conditions with a drying time of 10 minutes. The transfer resistance is judged as having an efficacy of 98%.

Furthermore, the individuals in the transfer-resistance test judged the product to be easy to spread and to give a uniform, adherent make-up effect with very good covering power and a pronounced color. The contour of the lips is sharp. The texture of the product is judged to be fluid and pleasant to apply. Removal of the make-up was carried out with a standard make-up-removing product (Bifacil from Lancome) without leaving traces.

Example 3: Foundation

The following composition is prepared:

| | |
|---|---|
| dispersion of Example 1 (22.6% solids) | 82.0 g |
| Nylon powder | 8.0 g |
| yellow iron oxide | 1.1 g |
| yellow-brown iron oxide | 0.6 g |
| black iron oxide | 0.3 g |
| titanium oxide | 8.0 g |

The pigments/polymer ratio is 0.55.

A foundation is obtained which can be applied to the body, in particular to the neck, and the face. The make-up effect is natural, matt, water-resistant and has very good transfer-resistance properties.

Example 4: Lipstick

A lipstick in stick form, having the composition below, is prepared:

| | |
|---|---|
| polymer dispersion(*) | 48.3 g |
| parleam oil | 7 g |
| octyldodecanol | 3 g |
| PVP/eicosene | 4 g |
| DC Red 27 | 2.2 g |
| phenyltrimethicone | 7.0 g |

-continued

| | |
|---|---|
| DC Red 7 | 4.2 g |
| DC Red 36 | 1.12 g |
| black iron oxide | 0.08 g |
| brown iron oxide | 2.4 g |
| polyethylene wax (Poly wax 500) | 20.7 g |

The polymer is prepared according to Example 1 with 95% methyl acrylate and 5% acrylic acid. The pigments/polymer ratio is 0.9.

The composition is prepared as follows: grinding of the pigments in the oils, which are heated gently; addition of the polyethylene wax at 100° C.; slight cooling, followed by addition of the polymer dispersion and, lastly, casting in a suitable mold in order to form a stick of lipstick.

A sensory test was carried out with this lipstick on several individuals, in comparison with a lipstick of the state of the art (Colour Endure from L'Oréal). The transfer-resistance test was carried out under the following conditions: application of the product to the lips, drying in the open air for 2 minutes and then application of the lips against a filter paper. This test was repeated under the same conditions with a drying time of 10 minutes.

The 2 products are equally easy to apply. The action of applying the make-up is more precise with the stick of the invention, since the product is more rigid. The make-up effect is judged to be homogeneous for the 2 products, but livelier and shinier with the stick of the invention. It is non-sticky for the two products, has a light sensation and does not feel tight. The transfer effect is less noticeable with the stick of the invention, given that the known product already had very good transfer-resistance properties. Removal of the make-up is easy for the two products, and no trace is left on the lips.

Obviously, numerous modifications and variations of the present invention are possible in light of the above teachings. It is therefore to be understood that within the scope of the appended claims, the invention may be practiced otherwise than as specifically described herein.

This application is based on French Application Serial No. 97-16251, filed on Dec. 22, 1997, and incorporated herein by reference.

What is claimed is:

1. Non transfer cosmetic or hygienic composition suitable for applying to the skin, lips, or exoskeleton comprising:
    a liquid fatty phase,
    at least one dye selected from liposoluble dyes, pigments, pearlescent agents and mixture thereof and
    from 2 to 60% by weight, with respect to the total weight of said composition, of surface-stabilized polymer particles, which polymer particles are dispersed in said fatty phase and stabilized at their surface,
    wherein the polymer is selected from the group consisting of radical polymers, polycondensates and polymers of natural origin, and mixtures thereof.

2. The composition of claim 1, wherein the polymer can form a film.

3. The composition of claim 1, wherein the polymer is selected from the group consisting of polyurethanes, polyurethane-acrylics, polyureas, polyurea-polyurethanes, polyester-polyurethanes, polyether-polyurethanes, polyesters, polyesteramides, polyesters containing a fatty chain, alkyds, acrylic and/or vinyl polymers or copolymers, acrylic-silicone copolymers, polyacrylamides, silicone polymers, fluoro polymers, and mixtures thereof.

4. The composition of claim 1, wherein the liquid fatty phase comprises carbon-based, hydrocarbon-based, fluoro and/or silicone oils of mineral, animal, plant or synthetic origin, alone, or a mixture thereof.

5. The composition of claim 1, wherein the liquid fatty phase is selected from the group consisting of liquid paraffin, liquid petroleum jelly, mink oil, turtle oil, soybean oil, perhydrosqualene, sweet almond oil, beauty-leaf oil, palm oil, parleam oil, grapeseed oil, sesame oil, corn oil, rapeseed oil, sunflower oil, cottonseed oil, apricot oil, castor oil, avocado oil, jojoba oil, olive oil cereal germ oil, esters of lanolic acid, of oleic acid, of lauric acid or of stearic acid, fatty esters, higher fatty acids, higher fatty alcohols, silicone oils, which are optionally phenylated, or which are optionally substituted with aliphatic and/or aromatic groups or with functional groups selected from hydroxyl, thiol, and/or amino groups, polysiloxanes modified with fatty acids, fatty alcohols or polyoxyalkylenes, fluorosilicones, perfluoro oils, and volatile oils.

6. The composition of claim 1, wherein the liquid fatty phase is selected from the group consisting of:
   (a) non-aqueous liquid compounds with a global solubility parameter, according to the Hansen solubility space, of less than 17 $(MPa)^{1/2}$,
   (b) or monoalcohols with a global solubility parameter, according to the Hansen solubility space, of less than or equal to 20 $(MPa)^{1/2}$, and
   (c) mixtures thereof.

7. The composition of claim 1, wherein the fatty phase contains at least one oil which is volatile at room temperature.

8. The composition of claim 1, wherein the stabilizer is selected from the group consisting of block polymers, grafted polymers and random polymers, and mixtures thereof.

9. The composition of claim 1, wherein the stabilizer is selected from the group consisting of silicone polymers grafted with a hydrocarbon-based chain, hydrocarbon-based polymers grafted with a silicone chain, grafted copolymers having an insoluble skeleton of polyacrylic with soluble grafts of polyhydroxystearic acid block or grafted block copolymers comprising at least one block of polyorganosiloxane and at least one block of a radical polymer, block or grafted block copolymers comprising at least one block of polyorganosiloxane and at least one block of a polyether, copolymers of $C_1$–$C_4$ alkyl acrylates or methacrylates or of $C_8$–$C_{30}$ alkyl acrylates or methacrylates, block or grafted block copolymers comprising at least one block resulting from the polymerization of a monomer containing ethylenic bond(s) and at least one block of a vinyl polymer, block or grafted block copolymers comprising at least one block resulting from the polymerization of a monomer containing ethylenic bond(s) and at least one block of an acrylic polymer, block or grafted block copolymers comprising at least, one block resulting from the polymerization of a monomer containing ethylenic bond(s) and at least one block of a polyether.

10. The composition of claim 1, wherein the stabilizer is a block or grafted block polymer comprising at least one block resulting from the polymerization of a monomer containing ethylenic bond(s) and at least one block of a vinyl polymer.

11. The composition of claim 1, further comprising at least one additional fatty phase selected from the group consisting of waxes, gums and/or pasty fatty substances of plant, animal, mineral or synthetic origin, or which are silicone-based, and mixtures thereof.

12. The composition of claim 1, wherein the pulverulent compound and the polymer are present in a pigment(s)/polymer ratio of less than 1.

13. The composition of claim 1, wherein the pulverulent compound comprises up to 40% of the total weight of the composition.

14. The composition of claim 1, wherein the pulverulent compound comprises from 1 to 30% of the total weight of the composition.

15. The composition of claim 1, wherein the polymer comprises, as solids, up to 60% of the total weight of the composition.

16. The composition of claim 1, wherein the polymer comprises, as solids, from 12 to 60% of the total weight of the composition.

17. The composition of claim 1, wherein the liquid fatty phase contains at least one oil selected from the group consisting of $C_8$–$C_{16}$ isoparaffins and linear or cyclic silicones having from 2 to 7 silicon atoms, these silicones optionally including alkyl groups having from 1 to 10 carbon atoms, and mixtures thereof.

18. The composition of claim 1, which is in the form of a stick or tube, in the form of a supple paste with a dynamic viscosity at 25° C. of about 1 to 40 Pa.s, in the form of a dish, an oily gel, an oily liquid, a vesicle dispersion containing ionic and/or nonionic lipids.

19. The composition of claim 1, which is in anhydrous form.

20. The composition of claim 1, which is in the form of a care product and/or a make-up product for the skin and/or the lips.

21. The composition of claim 1, which is in the form of a cast product.

22. The composition of claim 1, which is in the form of a cast foundation, a cast blusher or eye shadow, a lipstick, a lipcare balm or base or a concealer product.

23. A method of producing the composition of claim 1, comprising combining the liquid fatty phase, the dye, and the polymer particles.

24. A method of forming a forming a film on skin or lips, comprising applying a film-forming effective amount of the composition of claim 1 to the skin or lips.

25. The composition according to claim 1, containing at least 3% by weight of said polymer particles.

26. The composition according to claim 1, containing at least 5% by weight of said polymer particles.

27. The composition according to claim 1, containing at least 12% by weight of said polymer particles.

28. The composition according to claim 1, containing at least 30% by weight of said polymer particles.

29. A method of limiting the transfer of a make-up or care composition from the skin or lips onto a support other than the skin or the lips, wherein the composition comprises a liquid fatty phase and at least one ingredient selected from the group consisting of cosmetic active agents, dermatological active agents, hygiene active agents, pharmaceutical active agents, and dyes comprising introducing into the liquid fatty phase from 2 to 60% by weight, with respect to the total weight of said composition, of surface-stabilized polymer particles, which polymer particles are dispersed in said fatty phase and stabilized at their surface, wherein the polymer is selected from the group consisting of radical polymers, polycondensates and polymers of natural origin, and mixtures thereof.

* * * * *